United States Patent
Mir et al.

(10) Patent No.: US 10,982,283 B2
(45) Date of Patent: Apr. 20, 2021

(54) INDICES OF MICROBIAL DIVERSITY RELATING TO HEALTH

(71) Applicant: Biome Health, Inc., Sunnyvale, CA (US)

(72) Inventors: Alain Mir, Castro Valley, CA (US); Harris Shapiro, San Leandro, CA (US); Ronald Avignone, San Francisco, CA (US); Mark Kelleher, Campbell, CA (US)

(73) Assignee: Biome Health, Inc., Sunnyvale, CA (US)

( * ) Notice: Subject to any disclaimer, the term of this patent is extended or adjusted under 35 U.S.C. 154(b) by 0 days.

(21) Appl. No.: 16/852,534

(22) Filed: Apr. 19, 2020

(65) Prior Publication Data

US 2020/0270699 A1 Aug. 27, 2020

Related U.S. Application Data

(63) Continuation of application No. PCT/US2020/019398, filed on Feb. 23, 2020.

(60) Provisional application No. 62/809,873, filed on Feb. 25, 2019.

(51) Int. Cl.

| | | |
|---|---|---|
| *C12Q 1/6883* | (2018.01) | |
| *G16B 35/20* | (2019.01) | |
| *G16B 30/00* | (2019.01) | |
| *G16H 10/40* | (2018.01) | |
| *G16B 40/00* | (2019.01) | |
| *G16B 10/00* | (2019.01) | |
| *G16H 20/60* | (2018.01) | |
| *C12Q 1/6888* | (2018.01) | |
| *G16H 50/30* | (2018.01) | |

(52) U.S. Cl.
CPC ......... *C12Q 1/6883* (2013.01); *C12Q 1/6888* (2013.01); *G16B 10/00* (2019.02); *G16B 30/00* (2019.02); *G16B 35/20* (2019.02); *G16B 40/00* (2019.02); *G16H 10/40* (2018.01); *G16H 20/60* (2018.01); *G16H 50/30* (2018.01)

(58) Field of Classification Search
CPC .... C12Q 1/6883; C12Q 1/6888; G16H 10/40; G16H 20/60; G16B 10/10; G16B 40/00; G16B 35/20; G16B 30/00
See application file for complete search history.

(56) References Cited

U.S. PATENT DOCUMENTS

| | | | |
|---|---|---|---|
| 10,346,588 B2 | 7/2019 | Apte et al. | |
| 10,360,346 B2 | 7/2019 | Apte et al. | |
| 10,360,347 B2 | 7/2019 | Apte et al. | |
| 10,380,325 B2 | 8/2019 | Apte et al. | |
| 2014/0136120 A1 | 5/2014 | Colwell et al. | |
| 2015/0317444 A1 | 11/2015 | Backhed et al. | |
| 2016/0228003 A1* | 8/2016 | Apte | G16B 40/00 |
| 2018/0122510 A1* | 5/2018 | Apte | G16B 50/00 |
| 2018/0327812 A1 | 11/2018 | Jain | |
| 2019/0050534 A1* | 2/2019 | Apte | C12Q 1/6888 |

FOREIGN PATENT DOCUMENTS

| | | |
|---|---|---|
| WO | WO 2016/079731 | 5/2016 |
| WO | WO 2017/044871 | 3/2017 |
| WO | WO 2019/022790 | 1/2019 |

OTHER PUBLICATIONS

MacLellan et al., The Impact of Exclusive Enteral Nutrition (EEN) on the Gut Microbiome in Crohn's Disease: A review, 2017, Nutrients, 9(447), p. 1-14 (Year: 2017).*
Paliy et al., Application of phylogenetic microarrays to interrogation of human microbiota, 2012, FEMS Microbiol Ecol, 79, p. 2-11 (Year: 2012).*
Hartstra et al., Insights Into the Role of the Microbiome in Obesity and Type 2 Diabetes, 2015, Diabetes Care, 38, p. 159-165 (Year: 2015).*
Robertson et al., Resilience of the intestinal microbiota following pathogenic bacterial infection is independent of innate immunity mediated by NOD1 or NOD2, 2016, Microbes and Infection, 18, p. 460-471 (Year: 2016).*
Zhu et al., An Ensemble Feature Selection Method Based on Deep Forest for Microbiome-Wide Association Studies, 2018, IEEE, p. 248-253 (Year: 2018).*
Ai et al., Using Decision Tree Aggregation with Random Forest Model to Identify Gut Microbes Associated with Colorectal Cancer, Feb. 1, 2019, Genes, 10, p. 1-12 (Year: 2019).*
Matsuda et al., Establishment of an Analytical System for the Human Fecal Microbiota, Based on Reverse Transcription-Quantitative PCR Targeting of Multicopy rRNA molecules, 2009, Applied and Environmental Microbiology, p. 1961-1969 (Year: 2009).*

(Continued)

*Primary Examiner* — Olivia M. Wise
*Assistant Examiner* — Kaitlyn L Minchella

(57) ABSTRACT

Provided herein are methods for altering a health state of a subject by administering a wellness intervention to subjects found to have quantitative measures of microbial genera in the subject's microbiome that are associated with undesirable health states. Undesirable health states can be inferred by executing models that predict health states based on the quantitative measures, such as relative amounts of selected microbial genera to all microbes. Models are created by statistical methods that analyze datasets that include, for each of a plurality of subjects, verified health states and quantitative measures of each of a plurality of microbes classified at designated taxonomic levels, e.g., genus level.

24 Claims, 1 Drawing Sheet

(56) References Cited

OTHER PUBLICATIONS

Pollock et al., The Madness of Microbiome: Attempting to Find Consensus "Best Practice" for 16S Microbiome Studies, Apr. 2018, Applied and Environmental Microbiology, 84(7), p. 1-12 (Year: 2018).*

Yan et al., Microflora Disturbance during Progression of Glucose Intolerance and Effect of Sitagliptin: An Animal Study, 2016, Journal of Diabetes Research, p. 1-10 (Year: 2016).*

Jamar et al., Relationship between fatty acids intake and Clostridium coccoides in obese individuals with metabolic syndrome, 2018, Food Research International, 113, p. 86-92 (Year: 2018).*

Daousi et al., Prevalence of obesity in type 2 diabetes in secondary care: association with cardiovascular risk factors, 2006, Postgrad Med J, 82, p. 280-284 (Year: 2006).*

Chaudhary N, Sharma AK, Agarwal P, Gupta A, Sharma VK, "16S classifier: a tool for fast and accurate taxonomic classification of 16S rRNA hypervariable regions in metagenomic datasets", PLoS One. 2015;10(2):e0116106. Published Feb. 3, 2015.

Florian P Breitwieser et al., "A review of methods and databases for metagenomic classification and assembly," Briefings in Bioinformatics, vol. 20, Issue 4, Jul. 2019, pp. 1125-1136, doi.org/10.1093/bib/bbx120, Published: Sep. 23, 2017.

Bergstrom et al. FEMS Microbiology Letters, vol. 337, Issue 1, Dec. 1, 2012, pp. 38-47, https://doi.org/10.1111/1574-6968.12004.

Tottey et al. PLoS One. May 17, 2013;8(5):e62544. doi: 10.1371/journal.pone.0062544. Print 2013.

A. Loy. et al., "Oligonucleotide Microarray for 16S rRNA Gene-Based Detection of All Recognized Lineages of Sulfate-Reducing Prokaryotes in the Environment" Appl Environ Microbiol. Oct. 2002; 68(10): 5064-5081, doi: 10.1128/AEM.68.10.5064-5081. 2002, PMCID: PMC126405, PMID: 12324358.

Cole Jr, Wang Q, Cardenas E, Fish J, Chai B, et al. (2009) The Ribosomal Database Project: improved alignments and new tools for rRNA analysis. Nucleic acids research 37: D141-D145. 10.1093/nar/gkn879.

DeSantis TZ, Hugenholtz P, Larsen N, Rojas M, Brodie EL, et al. (2006) Greengenes, a chimera-checked 16S rRNA gene database and workbench compatible with ARB. Applied and environmental microbiology 72: 5069-5072. 10.1128/AEM.03006-05.

Pruesse E, Quast C, Knittel K, Fuchs BM, Ludwig W, et al. (2007) SILVA: a comprehensive online resource for quality checked and aligned ribosomal RNA sequence data compatible with ARB. Nucleic acids research 35: 7188-7196. 10.1093/nar/gkm864.

Mitra S, Stärk M, Huson DH (2011) Analysis of 16S rRNA environmental sequences using MEGAN. BMC genomics 12: S17 10.1186/1471-2164-12-S3-S17.

Caporaso JG, Bittinger K, Bushman FD, DeSantis TZ, Andersen GL, et al. (2010) PyNAST: a flexible tool for aligning sequences to a template alignment. Bioinformatics 26: 266-267. 10.1093/bioinformatics/btp636.

Caporaso JG, Kuczynski J, Stombaugh J, Bittinger K, Bushman FD, et al. (2010) QIIME allows analysis of high-throughput community sequencing data. Nature methods 7: 335-336. 10.1038/nmeth.f.303.

Shadnoush, M. et al. Effects of Probiotics on Gut Microbiota, Korean J. Gastroenterol; vol. 65, No. 4, 215-221; 2015.

PCT/US2020/019398—International Search Report dated Jun. 15, 2020.

\* cited by examiner

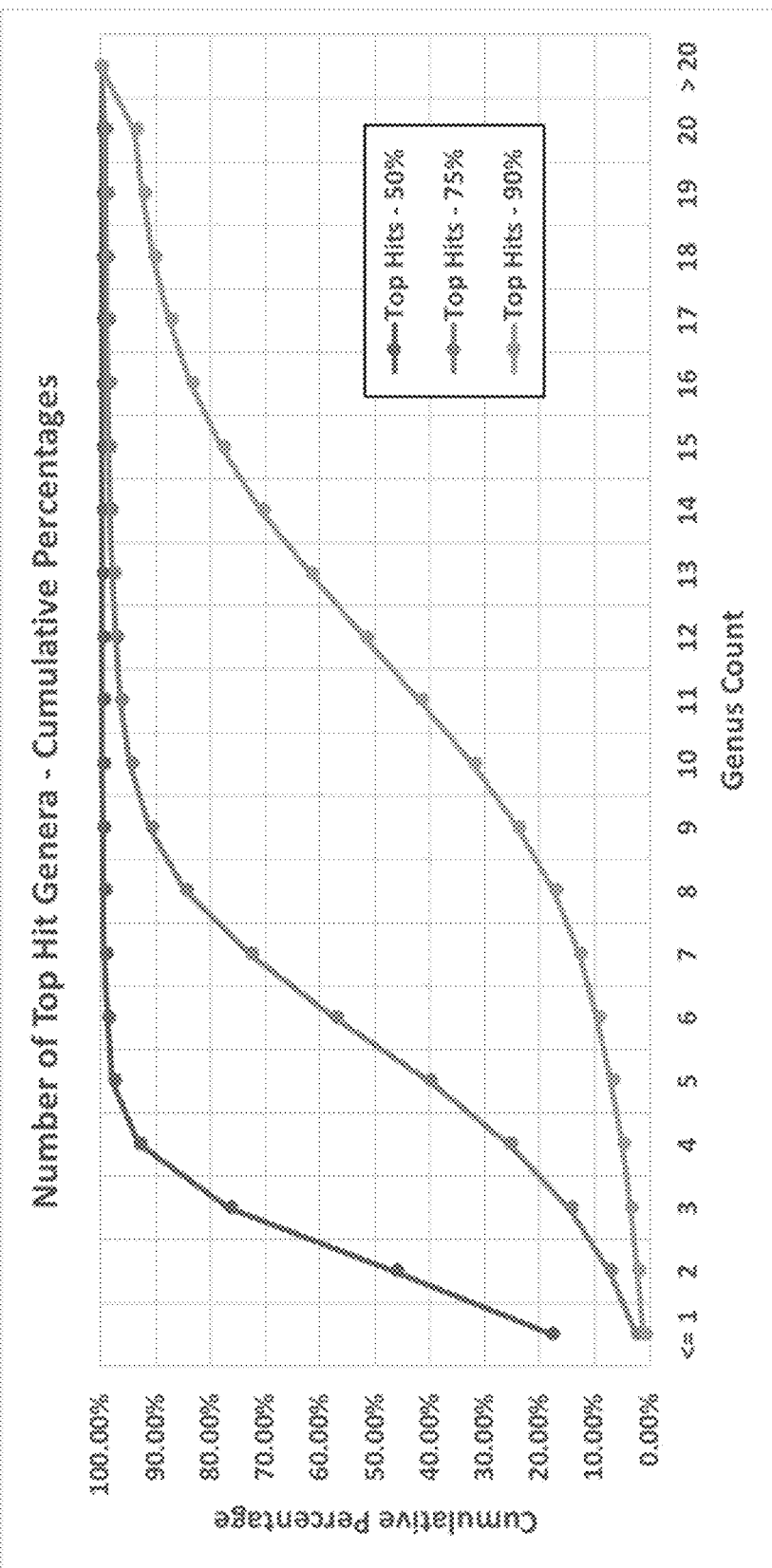

INDICES OF MICROBIAL DIVERSITY RELATING TO HEALTH

REFERENCE TO RELATED APPLICATIONS

This application claims the benefit of the priority date of International Patent Application PCT/US2020/019398, Filed Feb. 23, 2020 and U.S. Provisional application 62/809,873, filed Feb. 25, 2019, the contents of which are incorporated herein in their entirety by reference.

BACKGROUND

A goal of understanding microbiome studies is to reveal mechanisms of host genetic and environmental factors that shape the human microbiome. Insights gained from these types of studies may contribute to the development of improved health outcomes, including therapeutic strategies for modulating the microbiome composition in human health and disease states. However, despite significant public interest in this area of scientific investigation, conclusive data linking detection and causality remain elusive. Consequently, microbiome health claims study is fraught with correlative claims that are difficult to substantiate or link to a mechanism.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein:

FIG. 1 shows cumulative percentage of samples for which a given number of genera account for 50%, 75% and 90%, respectively of the total microbial biomass. The results show that in 97.8% of samples, 50% of total microbial biomass is accounted for by the top 5 genera. In 99.7% of samples, 50% of total microbial biomass is accounted for by the top 10 genera. In over 95% of samples, 75% of total microbial biomass is accounted for by the top 11 genera. In over 90% of samples, 90% of total microbial biomass is accounted for by the top 18 genera.

SUMMARY

A statistically significant correlation between quantities of fecal microbiome at the genus level and health conditions such as diabetes, body mass index, and dysbiosis, has been found. It has been found that microbial diversity is captured by relatively few genera. This concept has been used to aggregate analyses and identify major trends. This ability can be used to design genera taxonomy and/or specific 16S specific primer sets targeting microorganisms associated with these diseases for use in nucleic acid amplification and detection strategies permitting detection of specific high human health value targets associated with the above diseases. This further provides generic and/or actionable advice guidance to test result recipients. These results suggest that health practices that may ameliorate the health status of subjects either via exercise, diet or healthy eating practices may be valuable to pursue.

Provided herein are methods of developing mathematical models for inferring the status of a health condition in a subject. The methods involve providing a training dataset that includes data on a plurality of subjects. The data for each subject includes: (1) status of the health condition as verified by a medical practitioner, and (2) quantitative measures of each of plurality of gut microorganisms for which genus is provided or can be determined. The training data set is used to train the learning algorithm to generate a model that infers the state of an individual based on quantities of microorganisms the genus level.

Such models can be used in the methods of predicting or inferring a health state of an individual. Such methods involve providing from the individual a gut, vaginal canal, endometrial cavity, saliva, cell bound or cell containing or other biological fluid derived microbiome sample, for example, a fecal sample. From the sample is determined relative amounts of microbes from specified genera to total microbes. The specified genera are those used by the model to infer the health state in question. Quantitative measures of the specified genera can be determined, for example, by selective amplification of 16S RNA characteristic of each genus in the group of genera. For example, the specified genera can be quantified using qPCR or sequencing methodologies.

In one aspect provided herein is a method comprising: a) predicting a state of a health condition in a subject by: i) providing a microbiome sample (e.g., a gut, vaginal canal, endometrial cavity, saliva, cell bound or cell containing or other biological fluid derived microbiome sample) from a subject; ii) determining, from the sample, a quantitative measure of microbes in one or a plurality of selected microbial genera; and iii) applying a model to the quantitative measure to predict a state of the health condition; and b) recommending or administering to the subject an intervention selected from a food, a supplement, a probiotic, a lifestyle change or a pharmaceutical drug in an amount or degree sufficient to alter or maintain the state of the health condition. In one embodiment the state of the health condition is given as a score, and altering the state of the health conditions comprises altering the score. In another embodiment the method further comprises monitoring the state of the health condition in the subject over a period of time by repeating operations (i), (ii) and (ii) one or a plurality of times. In another embodiment the health condition is overweight Body Mass Index with Type II diabetes, and the selected microbial genus is taxonomic grouping "929". In another embodiment the quantitative measure is a relative amount of microbes belonging to taxonomic grouping "929" to total microbes. In another embodiment the model predicts that overweight Body Mass Index with Type II diabetes is present when the relative amount is above a threshold percent. In another embodiment the health condition is normal BMI with ulcerative colitis, and the selected microbial genus is taxonomic grouping "327". In another embodiment the quantitative measure is a relative amount of microbes belonging to taxonomic grouping "327" to total microbes. In another embodiment the model predicts that normal BMI with ulcerative colitis is present when the relative amount is above a threshold percent. the health condition is overweight Body Mass Index with Type II diabetes, and the selected microbial genus is taxonomic grouping "878". the quantitative measure is a relative amount of microbes belonging to taxonomic grouping "878" to total microbes.

In another aspect provided herein is a method comprising: a) accessing by computer, a dataset comprising, for each of a plurality of subjects, (1) a medically verified state of one or a plurality of health conditions, and (2) quantitative measures of amounts of microbes belonging to one or a plurality of selected microbial genera in a microbiome of the subject; and b) performing statistical analysis on the dataset to develop a model that predicts the state of the health condition in a subject based on the quantitative measures. In one embodiment the quantitative measure comprises relative amount of microbes belonging to the genus, e.g., compared to all microbes. In another embodiment the model predicts the state of the health condition based on the relative amount of a single microbial genus compared with total amount of microbes. In another embodiment the quantitative measure comprises an absolute amount of microbes belonging to the genus. In another embodiment the microbiome is a gut or other sample site microbiome. In another embodiment the measures are determined from a feces sample from the subject. In another embodiment the plurality of subjects is at least any of 1000, 2000, 4000, 8000, 14,000 or 30,000 subjects. In another embodiment the subjects are animals, e.g., fish, avians, amphibians, reptiles, or mammals, e.g., humans. In another embodiment the dataset is provided by curating the American Gut Project database. In another embodiment the dataset is provided by: i) accessing a database comprising quantitative nucleic acid sequence information from microbes in a microbiome, e.g. a gut, vaginal canal, endometrial cavity, saliva, cell bound or cell containing or other biological fluid derived microbiome; and ii) assigning microbial taxonomic group identities at the genus level for microbes in the microbiome based on the nucleic acid sequence information. In another embodiment the quantitative nucleic acid sequence information comprises quantitative measures of 16S RNA, and the microbial taxonomic group identities are assigned, at least in part, based on 16S RNA sequences. In another embodiment microbial taxonomic group identities are based on the NCBI taxonomy database, the Disbiome database (disbiome.u-gent.be), the Microbiome Database (microbiomedb.org/mbio/app/) or the Integrated Microbial Genomes and Microbiomes database (img.jgi.doe.gov/). In another embodiment the health conditions are selected from underweight Body Mass Index ("BMI"), overweight Body Mass Index, normal Body Mass Index, obese Body Mass Index, normal Body Mass Index with Type II diabetes, overweight Body Mass Index with Type II diabetes, obese Body Mass Index with Type II diabetes, normal Body Mass Index with Type I diabetes, normal Body Mass Index with ulcerative colitis, and unknown Body Mass Index with otherwise presumed healthy. In another embodiment the state of the health condition is characterized as a binary (e.g., presence or absence), a probability (e.g., chance of presence or absence), a number (e.g., a measurement or a score on a scale) or a range (e.g., high, medium or low). In another embodiment the statistical analysis comprises a recursive statistical analysis. In another embodiment the statistical comprises: correlational, Pearson correlation, Spearman correlation, chi-square, comparison of means (e.g., paired T-test, independent T-test, ANOVA) regression analysis (e.g., simple regression, multiple regression, linear regression, non-linear regression, logistic regression, polynomial regression. stepwise regression, ridge regression, lasso regression, elasticnet regression) or non-parametric analysis (e.g., Wilcoxon rank-sum test, Wilcoxon sign-rank test, sign test). In another embodiment the statistical analysis is performed by a machine learning algorithm. In another embodiment the machine learning algorithm is a supervised or unsupervised machine learning algorithm, e.g., selected from artificial neural networks (e.g., back propagation networks), discriminant analyses (e.g., Bayesian classifier or Fischer analysis), support vector machines, decision trees (e.g., recursive partitioning processes such as CART—classification and regression trees), random forests), linear classifiers (e.g., multiple linear regression (MLR) or graphical anova), partial least squares (PLS) regression and principal components regression (PCR)), hierarchical clustering and cluster analysis. In another embodiment the model calculates a numerical score that reflects the relative amount of a set of one or more selected microbial genera to the total amount of microbes. In another embodiment the model predicts that the health condition is present if a number representing a relative amount of the one or more microbial genera is above a cutoff value. In another embodiment the model predicts that the health condition is not present if a number representing a relative amount of microbes belonging to a selected taxonomic genus is below a cutoff value. In another embodiment the cutoff value is set to produce a sensitivity, selectivity, positive predictive value or negative predictive value of at least any of 75%, 80%, 85%, 90%, 95%, 98% or 99%. In another embodiment the state of the health condition is represented by a measure of confidence of the prediction.

In another aspect provided herein is a method of predicting a state of a health condition in a subject comprising: a) providing a microbiome sample (e.g., a gut, vaginal canal, endometrial cavity, saliva, cell bound or cell containing or other biological fluid derived microbiome sample) from a subject; b) determining, from the sample, a quantitative measure of microbes in one or a plurality of selected microbial genera; and c) applying a model to the quantitative measure to predict a state of the health condition. In one embodiment the state of the health condition is characterized as a binary (e.g., presence or absence), a probability, a number (e.g., a measurement or a score on a scale) or a range (e.g., high, medium or low). In another embodiment the model predicts that the health condition is present if a number representing a relative amount of microbes belonging to a selected taxonomic genus is above a cutoff value. In another embodiment the cutoff value is set to produce a sensitivity, selectivity, positive predictive value or negative predictive value of at least any of 75%, 80%, 85%, 90%, 95%, 98% or 99%. In another embodiment the model predicts that the health condition is not present if a number representing a relative amount of microbes belonging to a selected taxonomic genus is below a cutoff value. In another embodiment the cutoff value is set to produce a sensitivity, selectivity, positive predictive value or negative predictive value of at least any of 75%, 80%, 85%, 90%, 95%, 98% or 99%. In another embodiment the quantitative measure is a relative amount of the selected microbial genera to all microbes in the sample. In another embodiment the model predicts state of the health condition based on a cut-off value, e.g., wherein a relative amount above the cut-off value predicts that the health state is present and a relative amount below the cut-off value predicts that the health state is not present. In another embodiment the health condition is overweight Body Mass Index with Type II diabetes, and the selected microbial genus is taxonomic grouping "929". In another embodiment the quantitative measure is a relative amount of microbes belonging to taxonomic grouping "929" to total microbes. In another embodiment the model predicts that overweight Body Mass Index with Type II diabetes is present when the relative amount is above a threshold percent. In another embodiment the health condition is normal BMI with ulcerative colitis, and the selected microbial genus is taxonomic grouping "327". In another embodiment the quantitative measure is a relative amount of microbes belonging to taxonomic grouping "327" to total microbes. In another embodiment the model predicts that normal BMI with ulcerative colitis is present when the relative amount is above a threshold percent. In another embodiment the health condition is overweight Body Mass Index with Type II diabetes, and the selected microbial genus is taxonomic grouping "878". In another embodiment the quantitative measure is a relative amount of microbes belonging to taxonomic grouping "878" to total microbes. In another embodiment the sample is selected from human excreta (e.g., feces (stool) or urine), blood, serum, plasma, saliva, or throat swab. In another embodiment determining the relative amount comprises performing qPCR, WGA, mass spectroscopy, microarray analysis or DNA or RNA sequencing, loop mediated isothermal amplification, nucleic acid sequence-based amplification, strand displacement amplification, multiple displacement amplification or other isothermal amplification methods on nucleic acids of microbes in the sample. In another embodiment determining the taxonomic grouping from the DNA sequences comprises analysis of microbial 16S RNA sequences. In another embodiment determining the relative amount comprises: (i) sequencing microbial nucleic acids from the sample to produce DNA sequence information; and (ii) determining from the DNA sequence information microbes belonging to the single microbial taxonomic grouping and their amounts relative to total microbes in the sample. In another embodiment the method further comprises determining taxonomic groupings of a plurality of other microbes in the sample. In another embodiment the determining the quantitative measure of the set of selected microbial genera comprises determining a quantitative measure of the set as a whole. In another embodiment determining the quantitative measures comprises: (i) performing qPCR to determine a quantitative measure of the single microbial taxonomic grouping in the sample; and (ii) performing qPCR to determine a quantitative measure of total microbes in the sample. In another embodiment the qPCR comprises use of primers that selectively amplify sequences of 16S RNA of the single microbial taxonomic grouping. In another embodiment the qPCR comprises multiplexed qPCR. In another embodiment determining the quantitative measures comprises: (i) performing microarray analysis. In another embodiment the state of the health condition is represented by a measure of confidence of the prediction. In another embodiment the method comprises executing by computer a model produced by a method as disclosed herein. In another embodiment the model is the product of a machine learning algorithm.

In another aspect provided herein is a method comprising administering to a subject predicted, by a method as disclosed herein to have a health condition in a certain state, a food, supplement, probiotic or lifestyle change in an amount sufficient to alter or maintain the state of a health condition.

In another aspect provided herein is a method comprising: a) predicting, by a method as described herein, a state of a health condition for a subject; and b) communicating over the Internet, to the subject, the state of the health condition.

In another aspect provided herein is a system comprising: (a) a computer comprising: (i) a processor; (ii) a memory, coupled to the processor, the memory including a quantitative measure of microbes in one or a plurality of selected microbial genera, and a model that, when executed, uses the quantitative measure or measures to predict a state of a health condition for the subject; and (iii) computer executable instructions for implementing the classification rule on the data. In one embodiment, the system further comprises: (b) a communications interface that communicates with the internet.

In another aspect provided herein is a method comprising: (a) receiving from a subject a sample comprising a microbiome of the subject; (b) predicting a health state of the subject by a method as described herein; (I) optionally developing a wellness intervention plan to address a present health state in the subject; and (c) outputting the prediction/ intervention plan to an electronic device accessible by the subject or administering the wellness intervention to the subject. In one embodiment, predicting comprises measuring nucleic acid sequences of a microbiome of the subject by: (i) isolating RNA from the sample; (ii) reverse transcribing the RNA into cDNA; (iii) obtaining sequence information from the cDNA by nucleic acid sequencing to produce sequence reads or microarray analysis. In another embodiment predicting comprises measuring nucleic acid sequences of a microbiome of the subject by: (i) isolating DNA from the sample; (ii) amplifying rRNA sequences from the isolated DNA; and (iii) obtaining sequence information from the amplified rRNA sequences by nucleic acid sequencing to produce sequence reads or microarray analysis. In another embodiments the method further comprises (iv) mapping the sequence reads to a reference database of microbial nucleotide sequences, such as genomic sequences, and (v) measuring absolute or relative amounts of sequence reads mapping to the database. In another embodiment, predicting comprises measuring nucleic acid sequences of a microbiome of the subject by: (i) amplifying nucleic acids in the sample corresponding to genera associated with the health condition (e.g., by fragmenting nucleic acids from the sample and using primer pairs that specifically or preferentially amplify nucleic acids having nucleotide sequences of the associated genus or genera to amplify such sequences from the sample); (ii) amplifying nucleic acids in the sample corresponding to total rRNA; and (iii) determining relative amounts of the amplified nucleic acids.

DETAILED DESCRIPTION

I. Introduction

Provided herein are methods of predicting the state of each of a variety of health conditions in a subject based on the population of microbes in the subject's microbiome (e.g., gut, vaginal canal, endometrial cavity, saliva, cell bound or cell containing or other biological fluid derived microbiome). More specifically, it has been found that states of a variety of health conditions are statistically associated with the relative amount of single microbial genera in the microbiome. Taxonomically, the genus level is a taxonomic grouping between family and species. It is the sixth level in the NCBI taxonomy catalog, the levels being: (1) kingdom, (2) phylum, (3) class, (4) order, (5) family, (6) genus and (7) species. NCBI taxonomy classifications can be found at the World Wide Web site ncbi.nlm.nih.gov/taxonomy. Other taxonomy databases include, for example, the Disbiome database (disbiome.ugent.be), the Microbiome Database (microbiomedb.org/mbio/app/) or the Integrated Microbial Genomes and Microbiomes database (imgjgi.doe.gov/). Accordingly, by determining quantitative measures of microbes of a single genus and total microbes in a microbiome sample, one can predict the state of a health condition based on the relative amounts.

Statistical or mathematical models are built in which parameters of health conditions are estimated. An individual operator, such as a health professional, or a computer, can apply the model to data measured from a test subject to predict the state of the health condition. Models can involve numerical values, such as percentages of microbes in a sample belonging to a particular genus. The model may predict the state of the health condition by determining whether a numerical value is above or below a set cutoff value. For example, a measured value above the cutoff value may predict that a particular health condition is present in the subject or that there is a particular confidence that the subject has a health condition. Cutoff values can be set to provide desired levels of various diagnostic measures such as sensitivity, specificity, positive predictive value or negative predictive value.

II. Model Development

Models are developed to predict states of health conditions based on types and amounts of microorganisms found in a microbiome (e.g., a gut, vaginal canal, endometrial cavity, saliva, cell bound or cell containing or other biological fluid derived microbiome) of a subject. Databases can be used as inputs for model building. Databases typically include data for each of a number of subjects. Data for each subject includes a state of one or a plurality of health conditions for the subject and quantitative measures of each of a plurality of microbes belonging to a designated taxonomic category.

A. Database

In particular, taxonomic classification at the genus level provides particularly powerful associations. In certain embodiments the database includes, for each subject, a quantitative measure of microorganisms belonging to designated genera. Alternatively, the database can include, for each subject, quantitative measures of microorganisms at the species level. Quantitative measures at the genus level can be derived from these measures by, for example, combining measures of all species belonging to a particular genus. In other embodiments, microorganisms can be designated to a higher taxonomic level such as, phylum, class, order and family. Again, the database can include quantitative measures of microorganisms in each category of a taxonomic level, e.g., microorganisms belonging to particular phyla. Or, quantitative measures of microorganisms belonging to various categories at a particular taxonomic level can be derived based on combinations of subdivisions.

Such databases, when used to train learning algorithms, are typically referred to as the training set or a training dataset.

1. Health Conditions

Health conditions inferred by the methods described herein include any health conditions diagnosable by a medical professional qualified to make the diagnosis, e.g., to enter the diagnosis on a medical record. Typically, the medical professional is a doctor, such as an M.D., a D.O. or a chiropractor. However, under appropriate circumstances the medical professional could be a nurse or dietary health practitioner. As used herein, the term "medically verified" refers to a medical diagnosis made by such a medical professional.

Examples of health conditions include, without limitation, underweight Body Mass Index ("BMI"), overweight Body Mass Index, normal Body Mass Index, obese Body Mass Index, normal Body Mass Index with Type II diabetes, overweight Body Mass Index with Type II diabetes, obese Body Mass Index with Type II diabetes, normal Body Mass Index with Type I diabetes, normal Body Mass Index with ulcerative colitis, and unknown Body Mass Index with otherwise presumed healthy. Each of these states can be part of a binary classification. For example, the classifications can be overweight BMI or not overweight BMI; normal BMI with type I diabetes or not normal BMI with type I diabetes. For adult men and women, a BMI between 18.5 and 24.9 is considered healthy. Underweight is defined as a BMI below 18.5. Overweight is defined as a BMI between 25.0 and 29.9; and a BMI of 30 or higher is considered obese.

A health condition can be considered to be a categorical variable or feature in a vector representing subject data. The state of the health condition can be represented by a value in the feature cell. This value can take any form that differentiates one or more states of the health condition. So, for example, the state of the health condition can be characterized as a binary (e.g., presence or absence), a number (e.g., a measurement or a score on a scale) or a range (e.g., high, medium or low). Designation of any state of health condition can implicitly differentiate that state from its opposite. So, for example, state "overweight Body Mass Index with Type II diabetes" is distinguished from a state which is not both of these. This includes, for example, not overweight body mass index and not type II diabetes, overweight body mass index but not type II diabetes and not overweight body mass index but type II diabetes. In other words, an inference of "overweight Body Mass Index with Type II diabetes" is distinguished from these other states. In certain embodiments, the health states distinguish between pathological and nonpathological states.

A state of a health condition can be expressed in a variety of ways. These include, without limitation, as a binary (e.g., presence ("having") or absence ("not having" or not") of the condition), a probability (e.g., probability that the condition is present or absent), a number or degree (e.g., a measurement or a score on a scale) or a range (e.g., high, medium or low).

2. Taxonomic Information

A database used to develop a model to predict state of the health condition based on relative amounts of microbes in the microbiome also includes quantitative measures of a plurality of microbes in the microbiome. Quantitative measures of microbes at the genus level can be specified in the database or derivable from it. For example, the database could contain, as features or variables, quantitative measures of microbes belonging to each genus measured. Alternatively, the database could contain, as features or variables, quantitative measures of microbes belonging to each species measured. Based on the genus to which species belong, quantitative measures of microbes belonging to each genus can be derived. Such taxonomic information can be included in the database. Accordingly, in certain embodiments, each microorganism is classified at each of a plurality of taxonomic levels, e.g., kingdom, phylum, class, order, family, genus and species.

In certain embodiments a database includes sequences of nucleic acids present in a microbiome sample. Such sequences can be used to determine a taxonomic classification from which the sequences derive. So, for example, the database may include sequences of microbial 16S RNA. 16S RNA sequences can be used to classify microorganisms to the species level. The American Gut Project database (humanfoodproject.com/americangut/), (github.com/biocore/American-Gut) and links therein includes amounts of 16S RNA sequences found in microbiome samples of subjects. Genus and species of microorganisms to which the sequences correspond can be derived using, e.g., the NCBI taxonomy database or the metadata deposited in The European Bioinformatics Institute.

Next Generation Sequencing ("NGS") technologies providing reads that typically target the short high variability regions of the 16S rRNA gene. This approach is enabled because the lengths of the different variable regions of the 16S rRNA gene lie in the range of 100-300 bp, readily covered using short paired-end reads produced by commonly used in many common NGS methods. Longer range reads using nanopore or single molecule long read type technology is also envisaged. Earlier technical approaches such as Sanger sequencing methodologies can also be used to generate this information over longer reads, albeit with significantly less depth of sequencing reads.

The taxonomic classification of 16S rRNA gene sequences is obtained using either a homology-based or prediction-based approach. Taxonomic approaches require the alignment of the target 16S rRNA sequence with the 16S rRNA sequences present in the reference databases such as Ribosomal Database Project (1) Green genes (2) and SILVA (3). Several homology-based pipelines to stream line taxonomic analysis of 16S rRNA obtained from metagenomic datasets and include: MEGAN (4), PyNAST (5) and possibly the most commonly used pipeline QIIME (6).

A review of these methodologies with respect to a more recent pipe line "16S Classifier" has recently been described in Chaudhary N, Sharma A K, Agarwal P, Gupta A, Sharma V K, "16S classifier: a tool for fast and accurate taxonomic classification of 16S rRNA hypervariable regions in metagenomic datasets", PLoS One. 2015; 10(2):e0116106. Published 2015 Feb. 3. Other classifiers are described in Florian P Breitwieser et al., "A review of methods and databases for metagenomic classification and assembly," Briefings in Bioinformatics, Volume 20, Issue 4, Jul. 2019, Pages 1125-1136, doi.org/10.1093/bib/bbx120, Published: 23 Sep. 2017.

The dataset comprises data on a plurality of individuals. Data on each individual can include the health state of one or a plurality of different health conditions. The data will also include quantitative measures of each of a plurality of microbes from the microbiome of each subject. The data preferably at least identifies the microbes at the genus level. This includes, for example, providing quantitative measures at the species level, so long as the genus of each species is, or can be identified. As used herein, the term "genus" refers to a taxonomic rank which above species and below family. As used herein, the term "quantitative measure" refers to presence or absence, absolute or relative amounts or concentrations, absolute or relative increases or decreases and discrete or continuous ranges (e.g., a number, a degree, a level, a threshold, a quantile or a bucket). In some embodiments, the quantitative measure can be an absolute value, a ratio, an average, a median, or a range of numbers.

A measurement of a variable, such as sequencing reads mapping to a position, can be any combination of numbers and words. A measure can be any scale, including nominal (e.g., name or category), ordinal (e.g., hierarchical order of categories), interval (distance between members of an order), ratio (interval compared to a meaningful "0"), or a cardinal number measurement that counts the number of things in a set. Measurements of a variable on a nominal scale indicate a name or category, e.g., category into which the sequencing read is classified. Measurements of a variable on an ordinal scale produce a ranking, such as "first", "second", "third". Measurements on a ratio scale include, for example, any measure on a pre-defined scale, absolute number of reads, normalized or estimated numbers, as well as statistical measurements such as frequency, mean, median, standard deviation, or quantile. Measurements that involve quantification are typically determined at the ratio scale level.

The database can be a public or a private data set. It will typically include data for at least any of 500, 1000, 2000, 4000, 8000, 12,000, 16,000, 20,000, 30,000, 40,000, or 80,000 individuals. Typically, the database will include a plurality of individuals for each of a plurality of different health states for any health condition. Furthermore, the plurality classified at each state will be sufficient to provide statistically meaningful differentiation of each health state.

Taxonomic groupings identified by number have the following taxonomy:
- 35: kingdom Archaea; phylum Euryarchaeota; class Methanobacteria; order Methanobacteriales; family Methanobacteriaceae; genus *Methanobrevibacter*
- 327 kingdom Bacteria; phylum Actinobacteria; class Actinobacteria; order Bifidobacteriales; family Bifidobacteriaceae; genus *Bifidobacterium*
- 421 kingdom Bacteria; phylum Bacteroidetes; class Bacteroidia; order Bacteroidales; family [Paraprevotellaceae]; genus [*Prevotella*]
- 878 kingdom Bacteria; phylum Firmicutes; class Bacilli; order Lactobacillales; family Lactobacillaceae; genus *Lactobacillus*
- 929 kingdom Bacteria; phylum Firmicutes; class Clostridia; order Clostridiales; family Lachnospiraceae; genus *Clostridium*
- 946 kingdom Bacteria; phylum Firmicutes; class Clostridia; order Clostridiales; family Lachnospiraceae; genus [*Ruminococcus*]
- 1050 kingdom Bacteria; phylum Firmicutes; class Erysipelotrichi; order Erysipelotrichales; family Erysipelotrichaceae; genus *Clostridium*
- 935 kingdom Bacteria; phylum Firmicutes; class Clostridia; order Clostridiales; family Lachnospiraceae; genus *Lachnobacterium*

It is understood that the taxonomic position of particular genera, or their names may be changed by taxonomists over time.

B. Statistical Analysis

The database, once provided, can be analyzed by any statistical method. The analysis will model the association between the variables and the state of the health condition. This can include estimating parameters of the data such as medians, means and standard deviations. The model, once prepared, can use measurements from test subjects to predict the state of health condition.

Typically, analysis involves statistical analysis of a sufficiently large number of samples to provide statistically meaningful results. Any statistical method known in the art can be used for this purpose. Such methods, or tools, include, without limitation, correlational, Pearson correlation, Spearman correlation, chi-square, comparison of means (e.g., paired T-test, independent T-test, ANOVA) regression analysis (e.g., simple regression, multiple regression, linear regression, non-linear regression, logistic regression, polynomial regression, stepwise regression, ridge regression, lasso regression, elasticnet regression) or nonparametric analysis (e.g., Wilcoxon rank-sum test, Wilcoxon sign-rank test, sign test). Such tools are included in commercially available statistical packages such as MATLAB, JMP Statistical Software and SAS. Such methods produce models or classifiers which one can use to classify a particular biomarker profile into a particular state.

Statistical analysis can be operator implemented or implemented by machine learning.

1. Machine Learning

In certain embodiments statistical analysis is enhanced through the use of machine learning tools. Such tools employ learning algorithms, in which the relevant variable or variables are measured in the different possible states, and patterns differentiating the states are determined and used to classify a test subject. Accordingly, any classification method of this disclosure can be developed by comparing measurements of one or more variables in subjects belonging to the various health condition states. This includes, for example, determining a relative amount of microorganisms belonging to a designated genus to an amount of all microorganisms in a sample, and using this measure to predict the state of the condition using a model as described herein.

A variety of machine learning algorithms can be used to infer a condition or state of a subject. Machine learning algorithms may be supervised or unsupervised. Learning algorithms include, for example, artificial neural networks (e.g., back propagation networks), discriminant analyses (e.g., Bayesian classifier or Fischer analysis), support vector machines, decision trees (e.g., recursive partitioning processes such as CART—classification and regression trees), random forests, linear classifiers (e.g., multiple linear regression (MLR), partial least squares (PLS) regression and principal components regression (PCR)), hierarchical clustering and cluster analysis.

The learning algorithm is programmed to train on data at the genus level. As discussed, the quantitative measures provided in the dataset may be presented at the genus level, or may be presented at the species level from which genus level information can be derived. For example, quantitative measures of amounts of a plurality of species belonging to the same genus can be combined to provide a single quantitative measure for the genus.

C. Model

The end product of statistical analysis is a mathematical model that predicts or infers a state of health condition ("health state") based on quantitative measures of microbes at the genus level. Such mathematical models can also be referred to as diagnostic models or classifiers. In certain embodiments the model generates a single score, such as a number. This number can be compared to a cutoff level, e.g., determined by the learning algorithm, to infer a health state. For example, if the number is above a cutoff, the individual a be classified as the health condition being present (the state of the health condition is "present").

A model may rely on a single genus for classification of a health condition into a health state, or may use a plurality of genera to do so. For example, the number of genera used by the model may be equal to, at least or no more than any of 1 genus or 2, 3, 4, 5, 6, 7, 8, 9, 10, 11 or 12 different genera.

A model can be selected which provides a prediction at a predetermined level of sensitivity, specificity, positive predictive value or negative predictive value. So, for example, if the classifier employs a cutoff, and a pathological state is inferred if a score is above the cutoff, then, the cutoff level may be raised to increase specificity or decreased to increase sensitivity.

The sensitivity of a test is the percentage of actual positives that test positive (TP [true positive]/(TP+FN [false negative]). The specificity of a test is the percentage of actual negatives that test negative (TN [true negative]/(FP [false positive]+TN). The positive predictive value of a test is the probability that a subject that tests positive is an actual positive (TP/(TP+FP)). The negative predictive value of a test is the probability that a subject that tests negative is an actual negative (TN/(FN+TN)). Accordingly, a classifier can be selected that has a sensitivity, specificity, positive predictive value or negative predictive value of at least any of 75%, 80%, 85%, 90%, 95%, 98% or 99%.

The model also can provide a confidence of the prediction.

A model can produce a result that is positively associated with one state of the health condition and negatively associated with other states. For example, a positive association predicts that a particular health state is present. A negative association predicts that a particular health state is not present.

III. Applying a Model to Predict a State of a Health Condition

Models developed as described herein can be used to predict health states of individual subjects. In certain embodiments the methods involve providing a sample comprising microbiota, e.g., gut microbiota, from a subject. For example, the sample can be a fecal sample. The sample is then processed to quantify the amounts of each of one or a plurality of specified microbial genera in the sample relative to the quantity of total microbes in the sample. A specified microbial genus can be a genus the quantities of which are associated with the health state. The test data generated could include quantitative measures of total microbes and each specified microbial genus in the sample. Alternatively, the test data could include quantitative measures of each of a number of genera not included among the specified genera, as well as quantitative measures of the specified genera.

A biological sample from a subject can comprise, for example, human excreta (e.g., feces (stool) or urine), blood, serum, plasma, saliva, or throat swab.

A. Determining Quantitative Amounts of Microbes in a Sample

Quantifying specific genera in a sample can include targeting the specified genera for amplification, e.g., by PCR. Specific genera can be targeted for amplification, for example, by using genus-specific 16S RNA amplification primers. Alternatively, a collection of species-specific primers for the designated genus can be used. Quantification can be performed, for example, by qPCR. In certain embodiments each specified genus can be quantified separately. In other embodiments, the collection of specified genera can be quantified together in a multiplexed process such as multiplexed qPCR.

1. DNA Sequencing

Nucleic acids to be sequenced can include both DNA and RNA. Sequencing nucleic acids typically involves converting raw nucleic acids into a form compatible with a high throughput sequencer. This may include, in the case of RNA, reverse transcribing RNA into DNA. It may also include providing adapter molecules on DNA molecules adapted for function with particular DNA sequencer.

Nucleic acids can be sequenced by any methods known in the art to produce sequence reads comprising nucleotide sequences. Typically, nucleic acid sequencing is performed by high throughput sequencing. High throughput sequencing refers to the simultaneous or near simultaneous sequencing of thousands of nucleic acid molecules. High throughput sequencing is sometimes referred to as "next generation sequencing" ("NGS") or "massively parallel sequencing". Platforms for high throughput sequencing can be any suitable platform and include, without limitation, massively parallel signature sequencing (MPSS), Polony sequencing, 454 pyrosequencing, Illumina (Solexa) sequencing, SOLiD sequencing, Ion Torrent semiconductor sequencing, DNA nanoball sequencing, Heliscope single molecule sequencing, single molecule real time (SMRT) sequencing (PacBio), and nanopore DNA sequencing (e.g., Oxford Nanopore). Use of barcodes, such as with 10× Genomics (Pleasanton, Calif.) sequencing methods also can be used. Raw sequence reads are typically subject to bioinformatic analysis to transform the data into a format more useful for study. For example, sequence reads may be quantified to determine absolute or relative numbers of molecules having the same nucleotide sequence or having been derived from the same gene or the same area of the genome. Sequence data can be further analyzed, for example, to determine quantitative measures (e.g., absolute or relative amounts) of microorganisms in specific categories at different taxonomic levels. This includes, for example, identification of different phyla, orders, classes, families, genera and/or species of microorganism.

Accordingly, quantitative information about specific sequences can be used to determine quantitative measures of microbes belonging to each of a plurality of groupings within a taxonomic level, for example quantitative measures of microbes belonging to different genera.

2. qPCR

In another embodiment, microbes belonging to specific taxonomic groups, e.g., genera, can be determined by qPCR of nucleic acid acids having sequences characteristic of the taxonomic group. Quantitative PCR (qPCR) (also referred to as real time PCR or RT-PCR) involve simplification of nucleic acids using amplification primers selected to amplify nucleic acids having predetermined sequences. Quantitative PCR also uses a detectable marker such as a fluorophore to measure production of amplified product. After each round of PCR, the amount of marker is detected. The original amount of particular nucleic acid sequences in a sample is a function of the number of PCR rounds required to achieve a certain signal strength. Detection can be performed by nonspecific detection. This can involve using a dye, such as SYBR green, that binds to double-stranded DNA. Alternatively, detection can be performed by specific detection. This can involve, using detectably tagged reporter probes that only bind to sequences of interest.

In the present methods PCR primers that specifically amplify sequences of specified genera can be used. Examples of these primers and sequences can be found using the high-throughput real-time quantitative PCR-based 'GUt Low-Density Array' (GULDA) primer set. See FEMS Microbiology Letters, Volume 337, Issue 1, 1 Dec. 2012, Pages 38-47, doi.org/10.1111/1574-6968.12004 and references therein, denoting important phyla, genera, species, or other taxonomic groups within the five predominant bacterial phyla of the gut. Other assays sets can be designed by practitioners versed in the PCR design optimization.

3. Microarray Analysis

In another embodiment, microbes can be quantified by microarray analysis. Microarrays are solid supports having, at specific addressable locations, probes that hybridize to specific nucleotide sequences. Nucleic acids, typically bearing a detectable label, from the samples are contacted with the microarray and allowed to hybridize with the probes. The strength of the signal at each addressable location is a function of the amount of nucleic acid in the sample. An operator can determine one or a plurality of probes in the microarray that hybridize to sequences of specific taxonomic groups. Based on signal provided by the microarray, amounts of nucleic acids derived from specific taxonomic groups can be determined. A human gut chip "HuGChip" for determining microbiome diversity at family level has been described PLoS One. 2013 May 17; 8(5):e62544. doi: 10.1371/journal.pone.0062544. Print 2013. Custom microbiota microarray based on the Affymetrix GeneChip platform and the PhyloChip assay (secondgenome.com/solutions/services/phylochip/) have also been generated at world wide web site aem.asm.org/content/75/11/3572. Axiom Microbiome arrays are also available from Thermo Fisher at world wide web site affymetrix.com/support/technical/byproduct.affx?product=axiom microbiome array.

4. Exemplary Methods

In one exemplary protocol, a stool sample from a subject is provided. Microbial cells are isolated from the sample. Total RNA is isolated from the sample by, for example, guanidinium isothiocyanate precipitation. RNA is reverse transcribed into cDNA. The preponderance of cellular RNA is rRNA and the removal of other RNA types is optional. cDNA can be analyzed by, DNA sequencing, qPCR or by microarray analysis. Microarrays for analyzing rRNA sequences are described in the literature. See, e.g., Alexander, L. et al., "Oligonucleotide Microarray for 16S rRNA Gene-Based Detection of All Recognized Lineages of Sulfate-Reducing Prokaryotes in the Environment" Appl Environ Microbiol. 2002 October; 68(10): 5064-5081, doi: 10.1128/AEM.68.10.5064-5081.2002, PMCID: PMC126405, PMID: 12324358.

In another exemplary protocol, a stool sample from a subject is provided. Microbial cells are isolated from the sample. Total DNA is isolated from the sample by standard methods. Sequences corresponding to rRNA can be amplified from the genomic DNA by, for example, universal rRNA primers. The amplified DNA can be processed for high throughput sequencing, qPCR or by microarray analysis.

In other exemplary embodiments, parallel amplification processes are performed. A first amplification amplifies all rRNA sequences in the sample. A second amplification process specifically amplifies rRNA sequences from diagnostic genera. The amounts of both can be compared to determine a relative amount of diagnostic sequences to total rRNA sequences.

B. Tests

The American Gut Project database, a public data base of fecal 16S RNA sequence data (>14,000 patients) with varying disease states, was examined. Data from patients whose information had not verified by a medical practitioner, or sets of patients where the cohort size questionnaire responses are too small to draw conclusions from, were excluded. The vast majority of 16S diversity between patients is captured by relatively few Genera, i.e., ~97.8% of samples have at least 50% of unique hits in <=5 Genera and 99.7% in <=10 hits. See, e.g. FIG. 1.

After grouping patients into 10 different health categories, the filtered data set was subjected to statistical analysis comparing inter-health categories via a least square means analysis of variance methodology.

1. Microbial Taxonomic Grouping is "929" is Positively Associated with Overweight Body Mass Index with Type II Diabetes Microbial taxonomic grouping "929" is associated with a positive diagnosis of overweight body mass index with type II diabetes. For example, a relative amount of grouping "929" to total microbes above a cutoff predicts this health state. Put another way, where the percent of taxonomic grouping "929" microbes in a gut microbiota sample is above the cutoff, one can predict the presence of overweight body mass Index with type II diabetes.

2. Microbial Taxonomic Grouping is "878" is Positively Associated with Overweight Body Mass Index with Type II Diabetes Microbial taxonomic grouping "878" is associated with a positive diagnosis of overweight body mass index with type II diabetes. For example, a relative amount of grouping "878" to total microbes above a cutoff predicts this health state. Put another way, where the percent of taxonomic grouping "878" microbes in a gut microbiota sample is above the cutoff, one can predict the presence of overweight body mass Index with type II diabetes.

3. Microbial Taxonomic Grouping is "327" is Positively Associated with Normal Body Mass Index with Ulcerative Colitis Microbial taxonomic grouping "327" is associated with a positive diagnosis of normal body mass Index with ulcerative colitis. For example, a relative amount of grouping "327" to total microbes above a cutoff predicts this health state. Put another way, where the percent of taxonomic grouping "327" microbes in a gut microbiota sample is above the cutoff, one can predict the presence of normal body mass Index with ulcerative colitis.

IV. Wellness and Therapeutic Interventions

The associations described herein between relative amounts of specified microbial genera and health states is useful in the prescription, administration and monitoring of interventions to alter or maintain these states. Such interventions include, without limitation, administration of a food, supplement or probiotic, or lifestyle change, any of which can be provided in an amount or degree sufficient to alter or maintain the state of a health condition. Such interventions may improve wellness of a subject and/or may produce a therapeutic effect. A wellness intervention (including therapeutic intervention) protocol designed to address a particular health condition can be referred to as a wellness intervention plan. Such a plan could include recommendations of exercise, foods, supplements, probiotics, or pharmaceuticals to include in a lifestyle or diet. It can further amounts, timing and/or duration of such interventions.

As used herein, the term "wellness intervention" refers to an intervention that improves wellness of a subject. Wellness can be defined objectively and subjectively.

As used herein, the terms "therapeutic intervention", "therapy" and "treatment" refer to an intervention that produces a therapeutic effect, (e.g., is "therapeutically effective"). Therapeutically effective interventions prevent, slow the progression of, delay the onset of symptoms of, improve the condition of (e.g., causes remission of), improve symptoms of, or cure a health condition. A therapeutic intervention can include, for example, administration of a treatment, administration of a pharmaceutical, or a biologic or nutraceutical substance with therapeutic intent. The response to a therapeutic intervention can be complete or partial. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques. Recognizing that certain sub-groups of subjects may not respond to a therapy, one measure of therapeutic effectiveness can be effectiveness for at least 90% of subjects undergoing the intervention over at least 100 subjects.

As used herein, the term "effective" as modifying a therapeutic intervention ("effective treatment" or "treatment effective to") or amount of a pharmaceutical drug ("effective amount"), refers to that treatment or amount to ameliorate a disorder, as described above. For example, for the given parameter, a therapeutically effective amount will show an increase or decrease in the parameter of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Thus, according to some methods a subject is first tested for a gut micro biomarker of health condition in a biological sample from the subject. A prediction of the state for a health condition or conditions is determined based on the results. Based on the prediction a decision can be made regarding the type, amount, route and timing of administering an optimally effective therapeutic intervention to the subject.

V. Computer Systems:

Provided herein are computer systems for carrying out processes described herein. Computer systems can include a processor and memory accessible by the processor. For example, the processor can be a central processing unit (CPU). Memory can be in tangible form, for example, read only memory or random-access memory. Memory can include machine executable code (e.g., software) that, when executed by the processor, carries out instructions in the code. The software can be, for example, a model as described herein.

The computer system can also include a communication interface (e.g., network adapter) for communicating with one or more other systems, and peripheral devices. The computer system can be in communication with a computer network, such as a local area network or the internet. The system can be in communication with the internet through, for example, a high-speed transmission network including, without limitation, Digital Subscriber Line (DSL), Cable Modem, Fiber, Wireless, Satellite and, Broadband over Powerlines (BPL).

The computer system can communicate with one or more remote computer systems through the network. Examples of remote computer systems include personal computers, tablets, smart phone, etc. Communication can be by way of a user interface, such as a graphical user interface.

Accordingly, after making a prediction of a health state as described herein, the prediction and/or a wellness intervention plan to address the condition can be communicated to a user through a communications network such as the internet, where it can be accessed by user, for example, in password-protected format. So, for example, a method can include: Receiving from a subject a sample comprising a microbiome of the subject; predicting a health state of the subject by a method as described herein; and outputting the prediction/intervention to an electronic device accessible by the subject. The electronic device can include, for example, a personal computer, a tablet, a smart phone, or a wearable device. More specifically, the method of predicting can include determining nucleic acid sequences of a microbiome of the subject by, for example, (i) amplifying nucleic acids in the sample corresponding to genera associated with the health condition (e.g., by fragmenting nucleic acids from the sample and using primer pairs that specifically or preferentially amplify nucleic acids having nucleotide sequences of the associated genus or genera to amplify such sequences from the sample); (ii) sequencing the amplified nucleic acids to produce sequence reads; (iii) mapping the sequence reads to a reference database of microbial nucleotide sequences, such as genomic sequences, and (iv) measuring absolute or relative amounts of sequence reads mapping to the database. Alternatively, after predicting the state of the health condition, a wellness intervention in line with a wellness plan to ameliorate the health condition can be administered to the subject.

REFERENCES

Cole J R, Wang Q, Cardenas E, Fish J, Chai B, et al. (2009) The Ribosomal Database Project: improved alignments and new tools for rRNA analysis. Nucleic acids research 37: D141-D145. 10.1093/nar/gkn879

DeSantis T Z, Hugenholtz P, Larsen N, Rojas M, Brodie E L, et al. (2006) Greengenes, a chimera-checked 16S rRNA gene database and workbench compatible with ARB. Applied and environmental microbiology 72: 5069-5072. 10.1128/AEM.03006-05

Pruesse E, Quast C, Knittel K, Fuchs B M, Ludwig W, et al. (2007) SILVA: a comprehensive online resource for quality checked and aligned ribosomal RNA sequence data compatible with ARB. Nucleic acids research 35: 7188-7196. 10.1093/nar/gkm864

Mitra S, Stark M, Huson D H (2011) Analysis of 16S rRNA environmental sequences using MEGAN. BMC genomics 12: S17 10.1186/1471-2164-12-S3-S17 [PMC free article] [PubMed] [CrossRef]

Caporaso J G, Bittinger K, Bushman F D, DeSantis T Z, Andersen G L, et al. (2010) PyNAST: a flexible tool for aligning sequences to a template alignment. Bioinformatics 26: 266-267. 10.1093/bioinformatics/btp636

Caporaso J G, Kuczynski J, Stombaugh J, Bittinger K, Bushman F D, et al. (2010) QIIME allows analysis of high-throughput community sequencing data. Nature methods 7: 335-336. 10.1038/nmeth.f.303

Chaudhary N, Sharma A K, Agarwal P, Gupta A, Sharma V K. 16S classifier: a tool for fast and accurate taxonomic classification of 16S rRNA hypervariable regions in metagenomic datasets. PLoS One. 2015; 10(2):e0116106. Published 2015 Feb. 3.

As used herein, the following meanings apply unless otherwise specified. The word "may" is used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

What is claimed is:

1. A method of treating a subject having overweight Body Mass Index with Type II diabetes comprising:
    a) identifying a human subject having overweight Body Mass Index with Type II diabetes, wherein identifying comprises:
        i) providing a microbiome sample from the human subject;
        ii) determining, from the sample, a quantitative measure of microbes in the sample, wherein the quantitative measure is a relative amount of microbes consisting of microbial genus Clostridium to total microbes; and
        iii) applying a model to the quantitative measure to diagnose overweight Body Mass Index with Type II diabetes; and
    b) for the subject so identified, administering a probiotic in an amount effective to treat the overweight Body Mass Index with Type II diabetes.

2. The method of claim 1, wherein the microbiome is a gut microbiome.

3. The method of claim 1, wherein determining the quantitative measure comprises performing qPCR, WGA, mass spectroscopy, microarray analysis or DNA or RNA sequencing, loop mediated isothermal amplification, nucleic acid sequence-based amplification, strand displacement amplification, multiple displacement amplification, or another isothermal amplification method on nucleic acids of microbes in the sample.

4. The method of claim 1, wherein the sample is selected from human excreta, blood, serum, plasma, saliva, or throat swab.

5. The method of claim 1, wherein determining the quantitative measure of microbes comprises:
    i) sequencing nucleic acids in the sample to produce quantitative nucleic acid sequence information; and
    ii) assigning microbial taxonomic group identities at the genus level for microbes in the microbiome based on the nucleic acid sequence information.

6. The method of claim 5, wherein the quantitative nucleic acid sequence information comprises quantitative measures of 16S RNA, and the microbial taxonomic group identities are assigned, at least in part, based on 16S RNA sequences.

7. The method of claim 1, wherein determining the quantitative measure comprises:
    (i) performing qPCR to determine a quantitative measure of microbial genus taxonomic grouping "929" (genus Clostridium) in the sample; and
    (ii) performing qPCR to determine a quantitative measure of total microbes in the sample.

8. The method of claim 7, wherein performing qPCR to determine a quantitative measure of microbial genus Clostridium in the sample comprises the use of primers that selectively amplify sequences of 16S RNA of microbial genus Clostridium.

9. The method of claim 1, wherein determining the quantitative measure comprises performing microarray analysis.

10. The method of claim 1, wherein determining the quantitative measure comprises measuring nucleic acid sequences of a microbiome of the subject by:
    (i) isolating RNA from the sample;

(ii) reverse transcribing the RNA into cDNA;
(iii) obtaining sequence information from the cDNA by nucleic acid sequencing to produce sequence reads or microarray analysis.

11. The method of claim 10, further comprising:
(iv) mapping the sequence reads to a reference database of microbial nucleotide sequences, and
(v) measuring amounts of sequence reads mapping to the database.

12. The method of claim 1, wherein determining the quantitative measure comprises measuring nucleic acid sequences of a microbiome of the subject by:
(i) isolating DNA from the sample;
(ii) amplifying rRNA sequences from the isolated DNA; and
(iii) obtaining sequence information from the amplified rRNA sequences by nucleic acid sequencing to produce sequence reads.

13. The method of claim 12, further comprising:
(iv) mapping the sequence reads to a reference database of microbial nucleotide sequences, and
(v) measuring sequence reads mapping to the database.

14. The method of claim 1, wherein determining the quantitative measure comprises measuring nucleic acid sequences of a microbiome of the subject by:
(i) amplifying nucleic acids in the sample corresponding to microbial genus *Clostridium*;
(ii) amplifying nucleic acids in the sample corresponding to total rRNA; and
(iii) determining relative amounts of the amplified nucleic acids.

15. The method of claim 1, wherein the model diagnoses that overweight Body Mass Index with Type II diabetes is present when the relative amount is above a threshold percent.

16. The method of claim 1, wherein the diagnosis of overweight Body Mass Index with Type II diabetes is characterized as a binary value, a probability, a number, or a range.

17. The method of claim 1, wherein the model diagnoses that overweight Body Mass Index with Type II diabetes is present if a number representing the relative amount of microbial genus *Clostridium* to the total amount of microbes is above a cutoff value.

18. The method of claim 1, wherein the diagnosis of overweight Body Mass Index with Type II diabetes is represented by a measure of confidence in the diagnosis.

19. The method of claim 1, wherein the model uses a statistical analysis selected from: correlational, Pearson correlation, Spearman correlation, chi-square, comparison of means, regression analysis, and non-parametric analysis.

20. The method of claim 1, wherein the model is the product of a machine learning algorithm.

21. The method of claim 1, further comprising monitoring the overweight Body Mass Index with Type II diabetes in the subject over a period of time by repeating operations (a), (b), and (c) one or a plurality of times.

22. The method of claim 1, wherein the sample comprises feces, and the quantitative measure is determined from rDNA in the sample.

23. The method of claim 22, wherein determining the quantitative measure comprises:
(i) performing qPCR to determine a quantitative measure of microbial genus *Clostridium* in the sample; and
(ii) performing qPCR to determine a quantitative measure of total microbes in the sample.

24. The method of claim 22, wherein determining the quantitative measure of microbes comprises:
i) sequencing nucleic acids in the sample to produce quantitative nucleic acid sequence information; and
ii) assigning microbial taxonomic group identities at the genus level for genus *Clostridium* microbes in the microbiome based on the nucleic acid sequence information.

* * * * *